United States Patent
Dosta et al.

(10) Patent No.: US 11,944,320 B2
(45) Date of Patent: Apr. 2, 2024

(54) SYSTEM FOR LEFT ATRIAL APPENDAGE ISOLATION AND CLIP DEVICE THEREFOR

(71) Applicants: Joint Stock Company 'ALTIMED', Osipovichi (BY); Anatoli D. Dosta, Minsk (BY); Aliaksandr S. Zhyhalkovich, Minsk (BY); Anton A. Dosta, Minsk (BY)

(72) Inventors: Anatoli D. Dosta, Minsk (BY); Aliaksandr S. Zhyhalkovich, Minsk (BY); Anton A. Dosta, Minsk (BY)

(73) Assignees: JOINT STOCK COMPANY 'ALTIMED', Osipovichi (BY); Anatoli D. Dosta, Minsk (BY); Aliaksandr S. Zhyhalkovich, Minsk (BY); Anton A. Dosta, Minsk (BY)

( * ) Notice: Subject to any disclaimer, the term of this patent is extended or adjusted under 35 U.S.C. 154(b) by 0 days.

(21) Appl. No.: 17/498,710

(22) Filed: Oct. 11, 2021

(65) Prior Publication Data
US 2022/0022880 A1   Jan. 27, 2022

Related U.S. Application Data

(63) Continuation of application No. PCT/BY2019/000003, filed on Apr. 10, 2019.

(51) Int. Cl.
*A61B 17/122*   (2006.01)
*A61B 17/128*   (2006.01)
*A61B 17/00*    (2006.01)

(52) U.S. Cl.
CPC ........ *A61B 17/122* (2013.01); *A61B 17/1285* (2013.01); *A61B 2017/00243* (2013.01); *A61B 2017/00853* (2013.01)

(58) Field of Classification Search
CPC .............. A61B 17/122; A61B 17/1285; A61B 2017/00243; A61B 2017/00853
See application file for complete search history.

(56) References Cited

U.S. PATENT DOCUMENTS

| 2007/0112365 A1 | 5/2007 | Hilal et al. |
| 2008/0208324 A1 | 8/2008 | Glithero et al. |

(Continued)

FOREIGN PATENT DOCUMENTS

| EP | 2517652 A1 | 10/2012 |
| RU | 2261057 C1 | 9/2005 |

(Continued)

OTHER PUBLICATIONS

International Search Report from PCT/BY2019/000003, dated Dec. 12, 2019, dated Jan. 2, 2020.

(Continued)

*Primary Examiner* — Brooke Labranche
(74) *Attorney, Agent, or Firm* — Patentbar International (57) ABSTRACT

The system and device ensure a smooth and shockless effect of changeover of the first and second jaws from the diverged position to the clamped position with the control option of the impact force upon closing. The left atrial appendage isolation system incorporates a clip device between the first and second jaws, a clamping device and a control device. The clip has a connecting device, the clamping element is configured to contain the first hinge. The connecting device comprises the second hinge, the first and second hinges being connected to the corresponding ends of the first jaw and are designed to rotate the specified first jaw relative to the second jaw made fixed, at an angle ranging from 0° to 180°. The first hinge is made controllable, the control device comprises the first hinge actuator adapted to couple detachably with tension to fit with the said first hinge.

11 Claims, 11 Drawing Sheets

(56) References Cited

U.S. PATENT DOCUMENTS

| | | | |
|---|---|---|---|
| 2010/0179570 A1* | 7/2010 | Privitera | A61B 17/122 606/157 |
| 2011/0226837 A1* | 9/2011 | Baxter, III | A61B 17/07207 227/175.1 |
| 2015/0173767 A1 | 6/2015 | Monti et al. | |
| 2015/0190135 A1 | 7/2015 | Ibrahim et al. | |

FOREIGN PATENT DOCUMENTS

| | | |
|---|---|---|
| WO | 2010/011661 | 1/2010 |
| WO | 2012130589 | 10/2012 |
| WO | 2015077528 | 5/2015 |

OTHER PUBLICATIONS

Encyclopedia of Polymers, vol. 3., 1998, pp. 644-647, Sovetskaya Encyclopedia Publishing House, Moscow.
Goriainova et al., Fluoroplastics In Mechanical Engineering, 1971, p. 15, Moscow.

* cited by examiner

1 - CMC - cardiomyocytes
A					B

Fig.14

1 - CMC - cardiomyocytes
A					B

Fig.15

2 - AChE

1 – CMC – cardiomyocytes

Fig.17

1 – CMC – cardiomyocytes

SYSTEM FOR LEFT ATRIAL APPENDAGE ISOLATION AND CLIP DEVICE THEREFOR

RELATED APPLICATIONS

This Application is a Continuation Application of International Application PCT/BY2019/000003, filed on Apr. 10, 2019, which is incorporated herein by reference in its entirety.

FIELD OF THE INVENTION

The invention refers to medical equipment, particularly to the technology for isolating the left atrial appendage (LAA) from the left atrium for the prevention of cardiogenic thromboembolisms using endovideosurgical manipulations.

BACKGROUND OF THE INVENTION

The left atrial appendage is reported to become a risk for heart thrombosis in 91% cases for patients with non-rheumatoid atrial fibrillation (AF) and in 43% cases for patients with rheumatic heart diseases.

12% to 28.7% of AF patients over 65 years of age suffer from thromboembolic strokes annually, which represents a major economic problem for the health care system and society as a whole.

For the prevention of cardiogenic thromboembolism in AF patients, operations are made to isolate the left atrium orifice, both in the open heart and thoracoscopically using endovideosurgical techniques.

For LAA isolation, a number of different clip designs are used with appropriate delivery systems, e.g., a loop-shaped clip [US2015/0190135, Jun. 25, 2015] or a stapled seam using stitching machines [WO2012/130589, Oct. 4, 2012]. The use of a loop and stitching machine to isolate the left atrial appendage from the left atrium features several disadvantages. When a loop is applied, LAA wall corrugates, the loop fails to be placed at the appendage base, but more distal from LAA base, which serves a background for thrombosis.

When using stitching devices, microbleeds occur along the suture line, requiring the evacuation of blood residues by suction. Foci of micronecrosis and microthrombus are often identified in the sewn suture line area. When stitching, the left atrial appendage tissue is crushed by the stitching machine, which sometimes leads to LAA self-amputation, accompanied by life-threatening bleeding.

Also well-known are designs of LAA isolation clips in the form of a bifurcated plug, made to push the device onto the indicated LAA base from the open side and to clamp it with an additional component, which is also pulled outwardly [RU2261057, Sep. 27, 2005], [EP2517652, Oct. 31, 2012], [WO2015/077528, May 28, 2015]. The disadvantage of this kind of device is the unevenness of LAA base isolation, possible partial "slipping" of LAA tissue from the open side of the clip.

The frame-shaped designs feature no disadvantages of the one-sided clip design [WO2010/011661, Jan. 28, 2010], [US2015/173767, Jun. 25, 2015]. Such designs require stitching to delivery devices and removal of the threads following the device application to LAA base, which makes the surgery process more complicated and increases the risk of injury during the operation.

The most similar technology for both the LAA isolation system and LAA isolation clip device is given in [US2015/173767, Jun. 26, 2015]. The known technical solution includes a clip device for LAA isolation, formed by first and second jaws, designed so that they are parallel in the closed position and overlap each other in length, and spring elements installed between the first ends of the first and second jaws and between the second ends of the first and second jaws, which are designed to move the first and second jaws from the diverged position to the clamping position and to hold the first and second jaws in the clamped position. The known technical solution also incorporates a control device configured to install the clip device so that LAA is positioned between the first and second jaws by using the frame to which the clip is attached, previously placed to the diverged position. To turn to the clamped position, the threads should be removed, then, under the action of spring elements, the jaws move to the clamped position, pressing the left atrial appendage base.

The disadvantages of this technical solution is, firstly, the sharp changeover (with a blow) of the first and second jaws from the diverged position to the clamped position under the action of spring elements, which can lead to LAA tissue injury and even to its amputation, and, secondly, unregulated force of compression of the jaws on LAA base, which can lead to LAA tissue necrosis and inflammatory processes.

SUMMARY OF THE INVENTION

This invention is aimed to create a system for left atrial appendage isolation with clip therefor to ensure a smooth and shockless effect of changeover of the first and second jaws from the diverged position to the clamping position with the control option of the impact force upon closing, as well as to mitigate the impact of the clamped position over time.

The set objective for the left atrial appendage isolation system, which incorporates a clip device formed by first and second jaws, designed so that they are parallel in the closed position and overlap each other in length, and clamping device installed between the first ends of the first and second jaws and between the second ends of the first and second jaws, which are designed to move the first and second jaws from the diverged position to the clamping position and to hold the first and second jaws in the clamped position, as well as configured to install the clip device so that LAA is positioned between the first and second jaws, is solved by equipping the clip with a connecting device, wherein the clamping element is designed to contain the first hinge, and the connecting device comprises the second hinge, the first and second hinges being connected to the corresponding ends of the first jaw and are designed to rotate the specified first jaw relative to the second jaw made fixed, at an angle ranging 0° to 180°, while the first hinge is made controllable and the control device comprises the first hinge actuator adapted to couple detachably with tension to fit with the said first hinge.

Preferably, the first and second ends of the second jaw are rigidly fixed in the clamping element and connecting device, respectively.

Each of the first and second jaws can have Π-shaped design, preferably made of a biocompatible metal coated with porous polytetrafluoroethylene.

The clamping element may comprise a collet on the first hinge, as well as a threaded lock nut mounted on the axis of the first hinge and configured to clamp the collet to avoid the relief motion, while the control device in such case is made with a second actuator configured to be detachable with the specified threaded lock nut.

The first actuator of the control device can be made in the form of a first elongated cylindrical element for applying rotational motion to said first hinge with controlled rotation of the first jaw relative to the second jaw, and the second actuator of the control device can be made in the form of a second elongated cylindrical element as a concentric tube installed over the first elongated cylindrical element to apply rotational motion on the specified threaded lock nut.

The first and second actuators of the control device can be equipped with first and second levers fixed at 90° angle, respectively, each shaped as a torque arm, with an option of controlled rotation of the respective actuator.

The first and second tubes of the actuators of the control device can be curved.

The set objective of the clip device for the left atrial appendage isolation formed by first and second jaws, designed so that they are parallel in the closed position and overlap each other in length, and clamping device installed between the first ends of the first and second jaws, which is designed to move the first and second jaws from the diverged position to the clamping position and to hold the first and second jaws in the clamped position, is solved by equipping the clip with a connecting device, wherein the clamping element is designed to contain the first hinge, and the connecting device comprises the second hinge, the first and second hinges being connected to the corresponding ends of the first jaw and are designed to rotate the specified first jaw relative to the second jaw made fixed, at an angle ranging 0° to 180°, while the first hinge is made controllable.

Preferably, the first and second ends of the second jaw are rigidly fixed in the clamping element and connecting device, respectively.

Each of the first and second jaws can have Π-shaped design, preferably made of a biocompatible metal coated with porous polytetrafluoroethylene.

The clamping element may integrate a collet on the first hinge, as well as a threaded lock nut mounted on the axis of the first hinge and configured to clamp the collet to avoid the relief motion.

BRIEF DESCRIPTION OF THE DRAWINGS

The essence of the claimed invention is explained in detail at the following non-restrictive drawings, where:

DETAILED DESCRIPTION OF THE PREFERRED EMBODIMENTS

Figure 1:
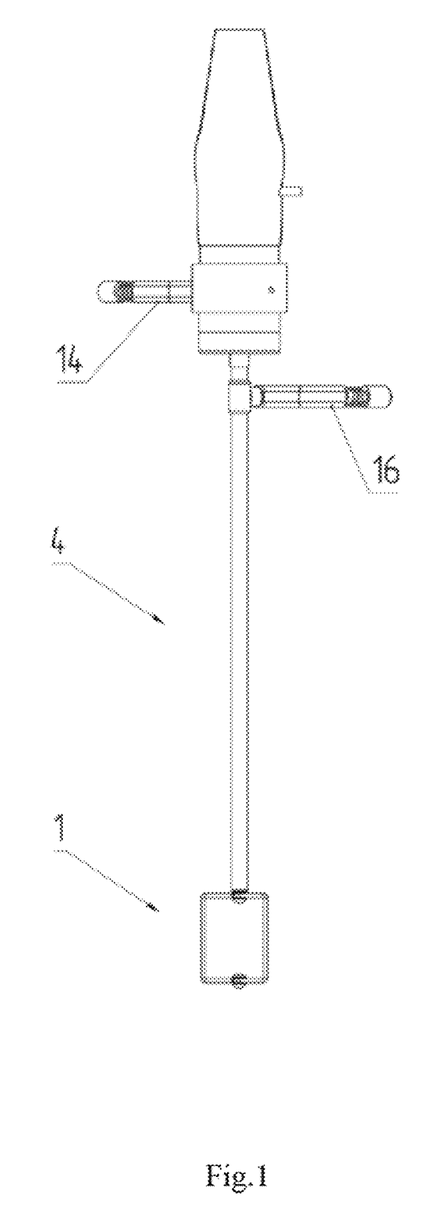
FIG. 1 shows a schematic general view of the claimed system with the clip device in the full-open position.
Figure 2:
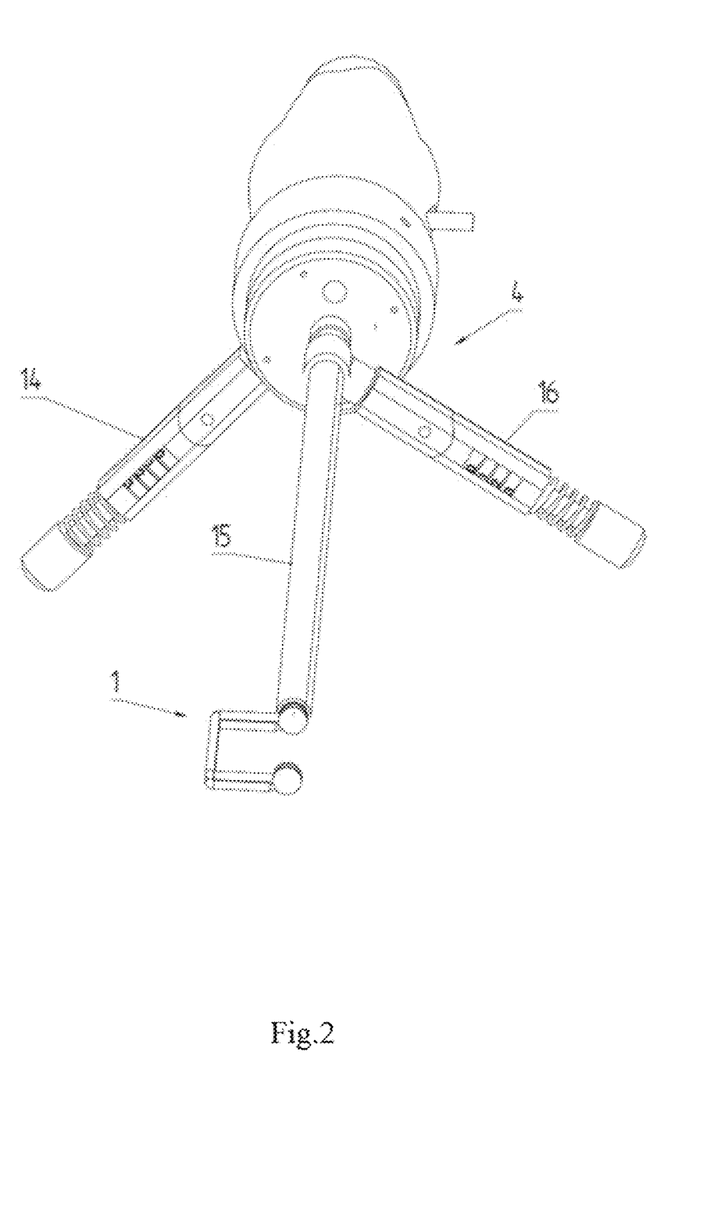
FIG. 2 shows a schematic general view of the claimed system with the clip in the full-closed position.

The system for LAA isolation, shown at FIGS. 1 and 2, contains a clip device 1, formed by the first 2 and second 3 jaws, made Π-shaped, as an example, so that they are parallel and overlap in length in their closed position (see FIG. 2), and the control device.

Figure 3:
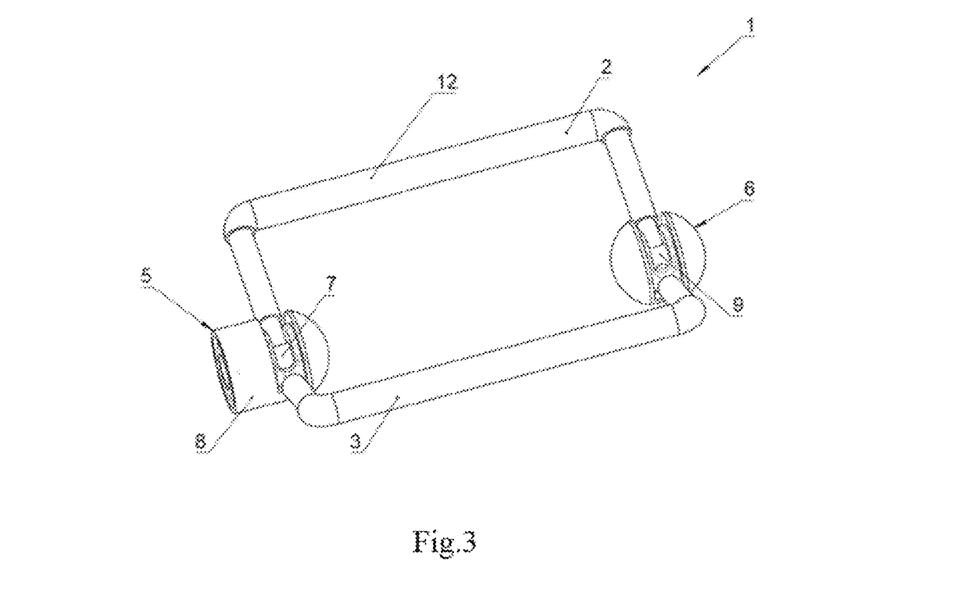
FIG. 3 shows a schematic general view of the dual-jaw clip device with PTFE coating.

Clip device 1, shown enlarged at FIG. 3, contains a clamping element 5 with first hinge 7, as well as a connecting device 6. The clamping element 5 is connected with the first ends of the first 2 and second 3 jaws so that the first end of the first jaw 2 is connected with the first hinge 7 installed in the housing 8 of the clamping element 5 to rotate the first jaw 2 relative to the second jaw 3 at an angle ranging 0° to 180°, while the first end of the second jaw 3 is rigidly fixed in the housing 8 of the clamping element 5. The second end of the first jaw 2 is connected to the second hinge 9 installed in the housing of the connecting device 6 so that the first jaw 2 can be rotated relative to the second jaw 3 at an angle ranging 0° to 180°, while the second end of the second jaw 3 is rigidly fixed in the housing of the connecting device 6.

Figure 4:
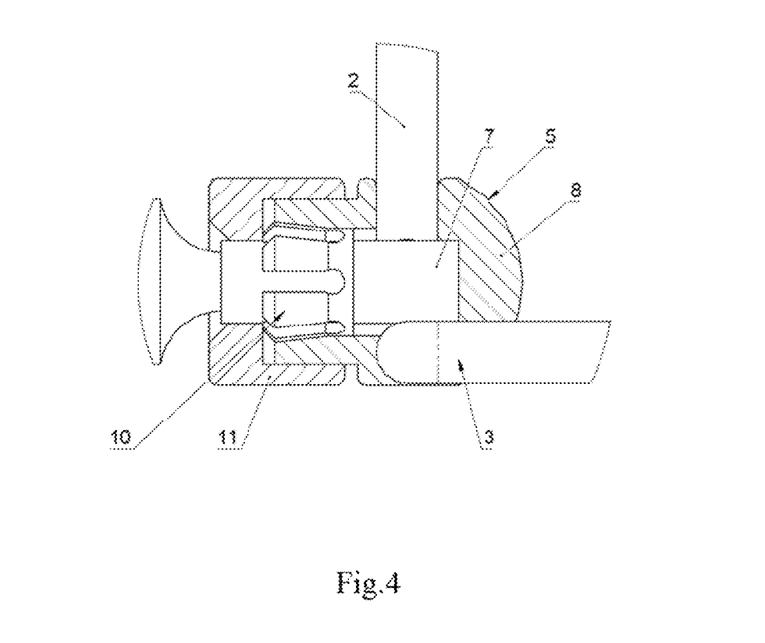
FIG. 4 schematically shows the mechanism for locking the jaw position of the clip device using a collet.
Figure 5:
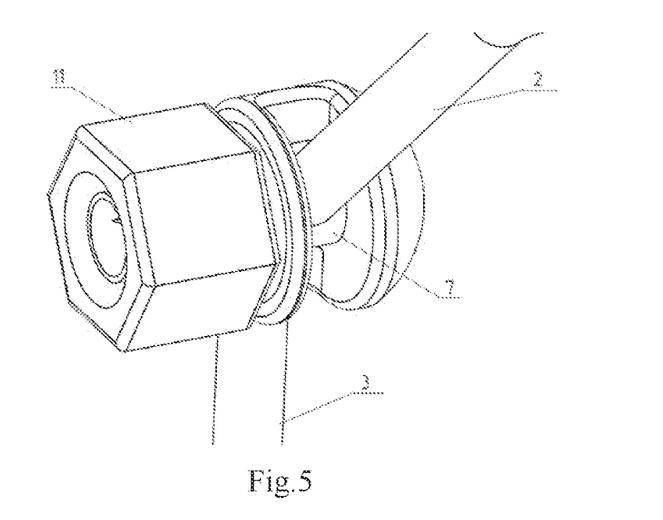
FIG. 5 schematically shows a threaded lock nut for the collet clamping.
Figure 6:
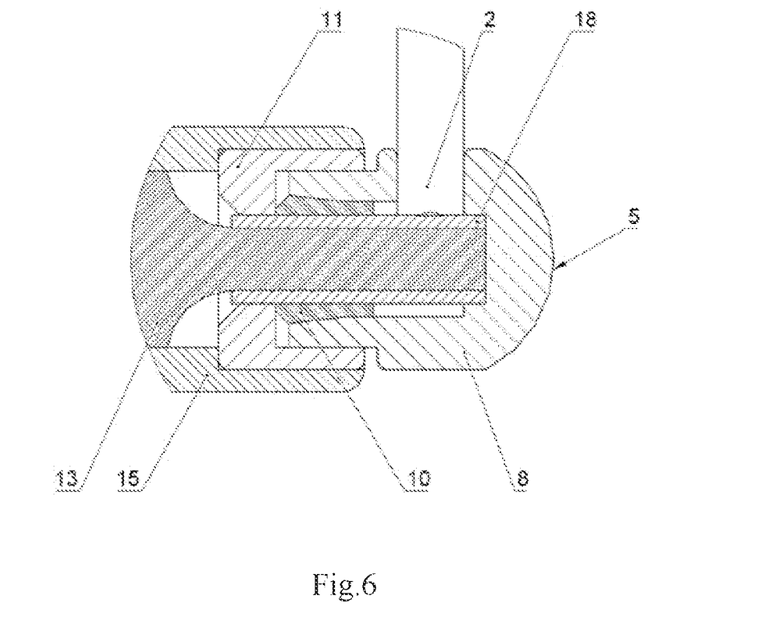
FIG. 6 schematically shows the clamping element of the claimed clip device connected to the control device, section view.

The clamping element 5 comprises a collet 10 located on the first hinge 7. As shown in FIGS. 4, 5 and 6, the clamping element 5 is equipped with a threaded lock hexagonal nut 11 (see FIG. 6) made to move along the thread (not shown at the drawings) in the housing 8 of the clamping element 5 for fixing the collet 10.

The first 2 and second 3 jaws are made of a biocompatible metal, e.g. titanium, with a porous PTFE coating 12, as schematically shown in FIG. 3.

Figure 8:
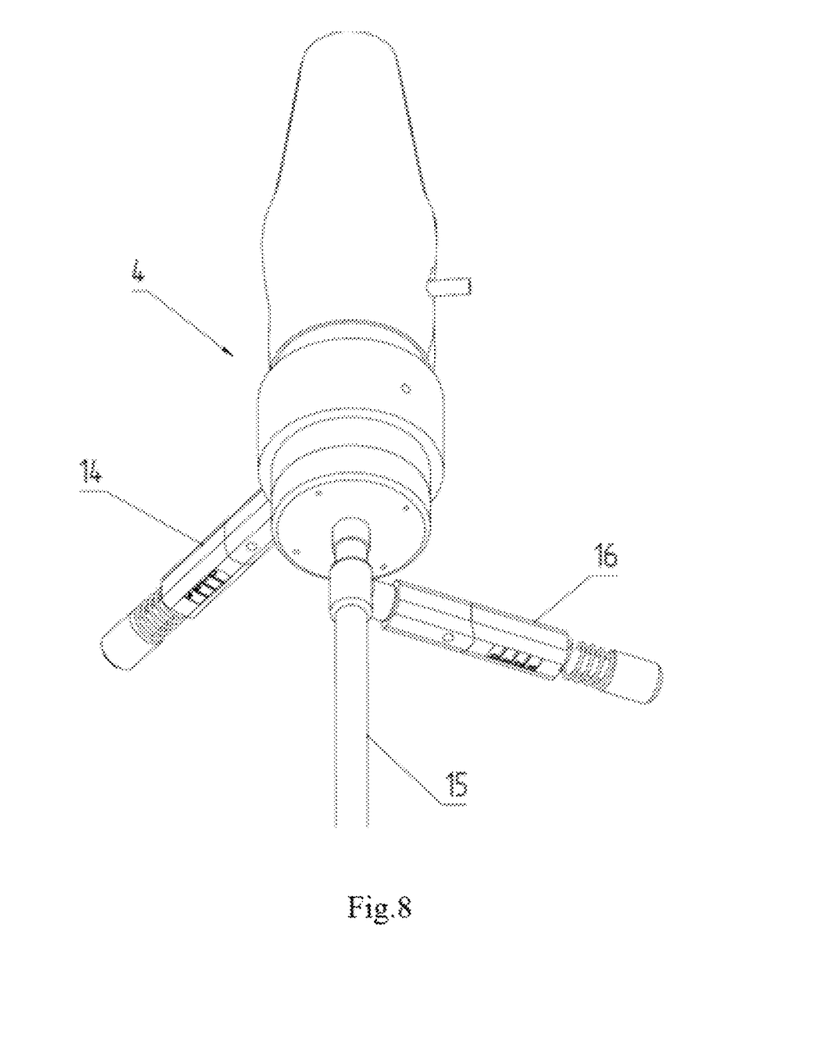
FIG. 8 schematically shows the controls of the control device.

The control device 4 (see FIG. 6, 8, 9) comprises the first actuator and the second actuator. The first actuator of the control device 4 is shaped as a first elongated cylindrical element, e.g., the first tube 13 with a lever 14 attached at 90° angle for applying torque to said first hinge. The first elongated cylindrical element of the first actuator can also be made in the form of a rod. The second actuator of the control device 4 is made in the form of a second tube 15 with a lever 16 fixed at 90° angle for applying torque to the said threaded lock nut 11. Levers 14 and 16 are each shaped as a torque arm, with an option of controlled rotation of the respective actuator (in the present example).

The proximal end 17 of the first tube 13 is made (in the present example) with a square cross-section, which can be detachably connected to the axis 18 of the first hinge 7, due to the tension created by the geometrical parameters of the proximal end 17, allowing both to hold the clip device 1 on the control device 4 and to disconnect, using the allowable force, with the control actuator, leaving the fixed clip device 1 on the body of the left atrium appendage 19.

The claimed system and clip device function as follows.

During the operation, prior to the application of the clip device, the control device 4 and the clip device 1 are taken from the sterile package. The control device 4 is attached to the clip device 1. For this purpose, the square cross-section proximal end 17 is fitted with an overpressure into the matching orifice, made in the longitudinal direction in the axis 18 of the first hinge 7. At the same time, the proximal end of the second tube 15 of the control device's second actuator is mounted on the nut 11.

Figure 9:
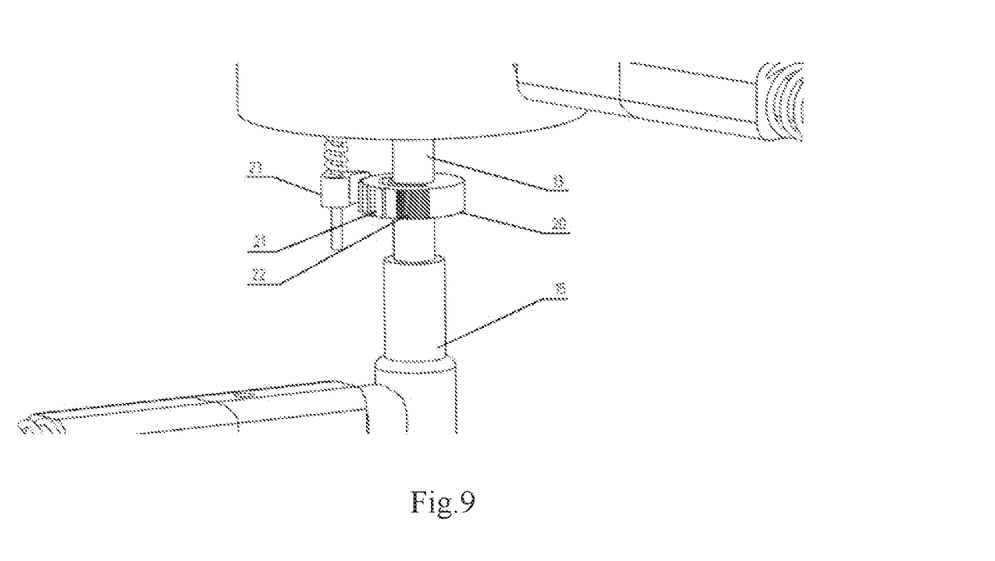
FIG. 9 schematically shows a system of gradual convergence of the clip jaws using a ratchet mechanism.

The convergence of the clip device's jaws 2 and 3 is performed gradually and with a controlled effort, not exceeding the allowable limits, thus avoiding the traumatic clamping of LAA body 19 with the jaws. For a gradual convergence of the jaws 2 and 3, a step mechanism is provided, made (in the present example) in the form of a ratchet—see FIG. 9, represented by a wheel 20 with cut-out grooves 21 with a large pitch for positioning the jaws on LAA and small grooves 22 for micro-movements when clamping the jaws, as well as a tooth 23 to lock the mechanism when it hits the grooves 21 or 22.

Figure 11:
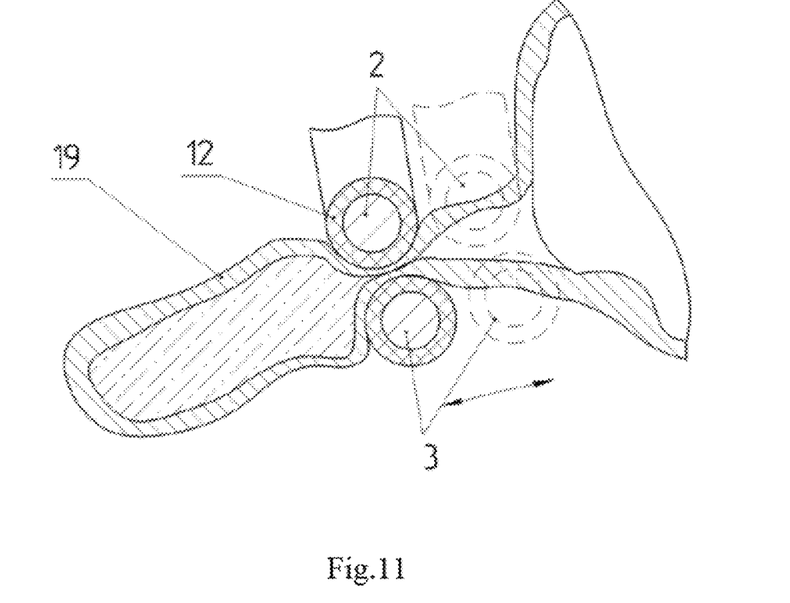
FIG. 11 shows a schematic general view of the left atrial appendage in the process of the clamp jaws positioning.
Figure 12:
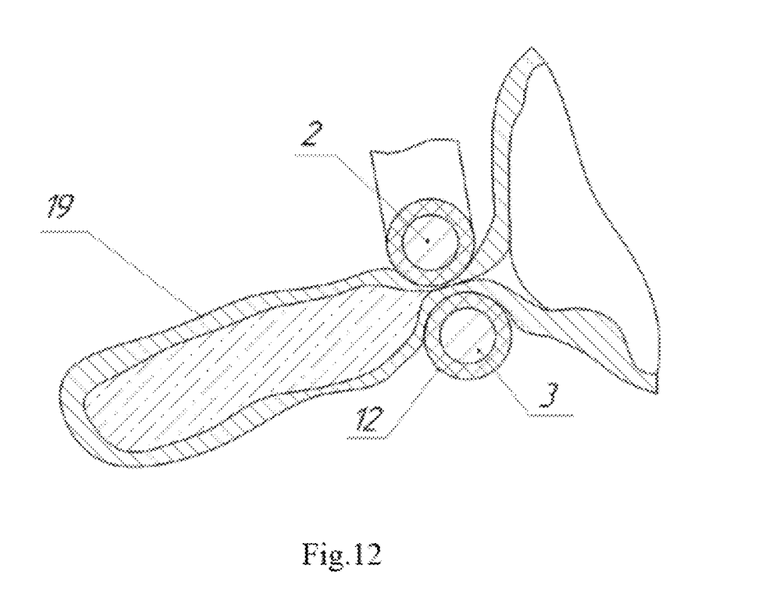
FIG. 12 shows a schematic general view of the left atrial appendage with the clip device in place.

The claimed clip device 1 can be clamped/decompressed for exact positioning and fixing of the clip jaws on LAA body—see FIG. 11,12.

Upon reaching the necessary clamping force of the jaws 2 and 3 on the appendage 19, the jaws are fixed in their position.

Figure 7:
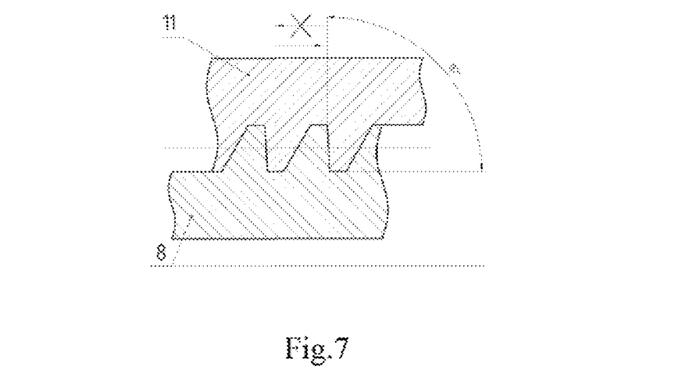
FIG. 7 schematically shows the threaded lock nut and casing of the clamping element.

For a strong fixation of the jaws 2 and 3 position relative to each other, as well as to avoid their release, the device uses the collet 10, tightened by the nut 11 (FIG. 4, 5, 6). By actuating the lever 16 of the second actuator of the control device 4, the rotation of the second tube 15 is imparted to transmit the torque to the said threaded lock nut 11. The nut 11 moves along the thread (not shown on the figures) inside the housing 8 of the element 5, advances on the collet 10, pressing it to the axis 18 and fixing the axis 18 of the hinge 7, and, therefore, avoiding the jaw 2 rotation. Since the thread on the nut 11 and the housing 8 are made with a locking feature, as shown in FIG. 7, the back motion of the nut is prevented, and any release of the installed clip device 1 is also avoided.

After fixing the clip device 1, the proximal end 17 is withdrawn from the hole in the axis 18 by force action on the lever 14 of the control device 4 and moving in the distal direction, and then, by moving the entire control device in the distal direction, the second tube 15 is withdrawn from the nut 11, and the control device is removed from the surgical field.

Process of Surgical Procedure

Figure 10:
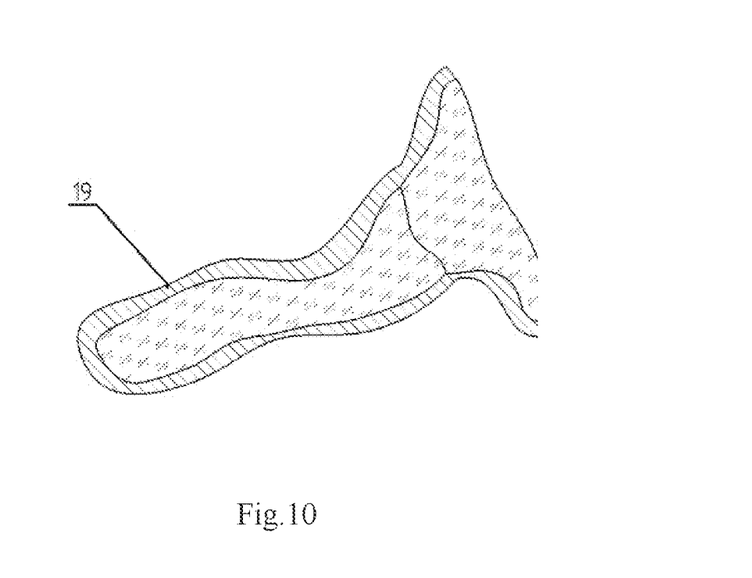
FIG. 10 shows a schematic general view of the left atrial appendage.

Open-heart surgery:

Following the cardiopulmonary bypass and cardioplegic cardiac arrest during open-heart surgery via sternotomy, enucleation and heart (left ventricle) rotation to the right shall be made for proper visualization of the appendage 19 (see FIG. 10). The clip device 1 is supplied in the full (sufficiently) open position (see FIGS. 1, 3 and 11), positioned and closed so that the jaws 2 and 3 are located at the appendage 19 base (see FIG. 12).

The clamping position control shall be effected by using transesophageal echocardiography.

Minimally invasive surgery:

Minithoracotomy or thoracoscopy is performed is such case. For thoracoscopy, a special endoscopic instrument shall be used for opening the pericardium, three thoracoports are to be made in the left half of the chest:
- the first thoracoport at $7^{th}$ intercostal space on the anterior axillary line,
- the second thoracoport at $4^{th}$ intercostal space in the mid-axillary line,
- the third thoracoport at $3^{rd}$ intercostal space on the anterior axillary line.

The pericardium shall be opened 1 cm below the phrenic nerve under the video control. The pericardium shall be taken by the holders and pulled apart for better access to the appendage 19.

The control device 4 with the clip device 1, preferably in the fully clamped position (see FIG. 2), shall be supplied through the lower thoracoport. By turning the first tube 13 under the actuation of the lever 14, the jaw 2 shall be taken aside from the jaw 3 to allow the required opening, up to 180°, preferably 120°.

No special tool-based manipulations are needed for the clip device 1 placement on the appendage 19 body, since the clip device 1 passes freely through the top of the appendage 19, and the gradual convergence of the jaw 2 to the jaw 3 (by turning the first tube 13 under the action of the lever 14 with controlled force) makes it possible to arrange the jaws 2 and 3 close to the appendage 19 base without any contact with the surrounding tissues and structures.

The clip device 1 placement and clamping is controlled by transesophageal Echo-CG.

The clip device 1 of the claimed design can be placed to the appendage 19 (including a thrombus-affected one), if the thrombus does not extend from LAA into the cavity of the left atrium beyond the jaws and does not exceed their width.

Should the initial implantation of the clip device 1 fail (see FIG. 11), it is possible to reposition the clip device 1 numerously. After the clip device 1 has been positioned properly (see FIG. 12), the fixation process is performed. The use of a torque actuator makes it possible to avoid pinching the appendage body, which may otherwise result in soft tissue necrosis.

For fixing the clip device 1, the second tube 15 of the control device 4 shall be rotated, thus allowing the threaded lock nut 11 to advance along the thread (not shown on the figures) inside the housing 8 of the clamping element until the collet 10 fixed on the first hinge 7 is locked. The thread (e.g. FIG. 7) prevents from motions in the direction opposite to winding, thus, the rotation of the first hinge 7, and, consequently, the retraction of the first jaw 2 from the second jaw 3 is prevented following the implantation of the clip device 1.

Then, the control device 4 shall be removed. For this purpose, the proximal end 17 of the first tube 13 is distally moved out of the hole in the axis 18, and then, by moving the entire control device in the distal direction, the second tube 15 is withdrawn from the nut 11, releasing the clip device 1 fixed on LAA body 19—see FIG. 12. Then, the control device 4 can be removed from the thoracoport.

Figure 13:
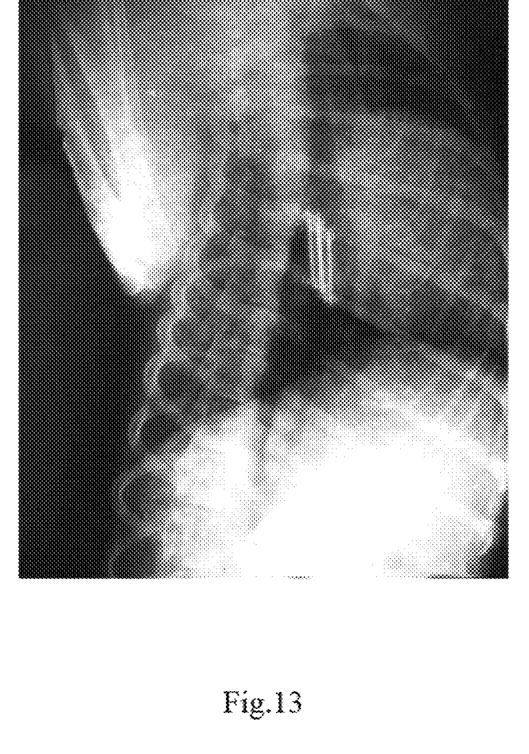
FIG. 13 shows the X-ray picture of the left atrial appendage with the clip device placed, the clip being made of titanium and coated with porous polytetrafluoroethylene (PTFE)

The clip device 1 remains fitted to the appendage 19 base (see FIG. 12, 13). Due to the phenomenon of PTFE recrystallization following the clamping of the clip device 4 jaws on LAA 19 benefits to the load relief on LAA tissue.

Polytetrafluoroethylene is a well-known material, used for many applications for a long time [Encyclopedia of Polymers, Vol. 3. Sovetskaya Encyclopedia Publishing House, Moscow, 1998, p. 644-647]. This aforesaid property of this material is also known as "cold flow under load", "creep" (same reference, p. 645) or "pseudo flow" [A. V. Goriainova et al. Fluoroplastics in mechanical engineering. M., p. 15]. This means that, even under minor mechanical loads at room temperature, a product made of PTFE is subject to recrystallization process, followed by internal deformations. Within 5-7 hours, polytetrafluoroethylene in contact with LAA tissue is deformed due to recrystallization, its thickness decreases, and the pressure on LAA surface decreases abruptly, with LAA isolation being preserved. The blood circulation in the LAA surface layer is fully restored, thus reducing the risk of infection, necrosis.

Then, LAA tissue penetrates inside the porous PTFE coating 12 of jaws 2, 3 of the clip device 1, thus forming a permanent connection and ensuring the reliability and durability of the left atrial appendage isolation.

Example 1

2 dogs weighing 15 kg and 15.6 kg. Premedication given on the operating table.

Operation process: The dog was laid on the right side, with its forelimbs placed apart and fixed. The operating field was treated by iodonates. In the $6^{th}$ intercostal space, a lateral thoracotomy of about 6.0 cm was performed. The lung was set aside with a special hook for accessing the pericardium.

The pericardium was opened by a T-shaped incision and taken on the handles. The left atrial appendage was visualized directly in the surgical wound. Using the grip, the appendage was inserted into the clip device 1, the latter was positioned at LAA base and fixed by controlled compression until the blood flow stopped (the appendage's apical part was cut to control the blood flow cessation).

No heart rhythm disturbances were noted (ECG control). The pericardial cavity was sutured. No drainage of cavities was made. The layer-by-layer wound closure with the left lung reexpansion was performed to avoid pneumothorax.

The implant was clearly visualized at LAA. The clip device 1 was made of titanium and covered with porous PTFE coating 12 (X-ray picture—see FIG. 13). The hematology analysis made it possible to assess the post-operation recovery dynamics.

An increase in band neutrophils and monocytes after 1 month post-operation evidenced that the tissue repair processes were accompanied by activation of the body protective functions. The eosinophil count normalized by the $7^{th}$ week, evidencing no allergic reactions, which is an important prognostic indicator of the implant survival rate. The placement of implants did not affect the platelet count in the dog's blood.

The sampling of heart tissues to study the peculiarities of the implant-surrounding tissue formation was made approximately 2 months following the operation, upon reaching normal hematological parameters.

Materials and Methods Used

The activity of enzymes characterizing the metabolic activity of cells, i.e. succinate and lactate dehydrogenase (SDH and LDH), was determined by Lloyd's method. The enzyme activity was estimated by the optical density of the reaction product in the cytoplasm of cells (formazan) using Image J data processing software. Microscopic examination, morphometry and microphotography were carried out using an MPV-2 light microscope with integrated software and computer (manufactured by Leitz, Germany).

The detection of AChE-positive nerve fibers in the myocardium was performed according to Karnovsky-Roots method, as modified by El-Badawi and Schenk. The final product of the reaction, which occurs with acetylcholinesterase enzyme participation, was determined in the form of copper ferrocyanide precipitates, which stain cholinergic nerve formations—nerve fibers and endings—in brown.

The detection of LDH and SDH enzymes was performed in cardiac myocytes of the atrial appendage and cardiomyocytes penetrating into porous PTFE coating of the clip jaws. The presence of enzymes in the myocardium was evidenced by a dark blue precipitate of formazan formed during the recovery of tetrazolium salts and localized in the sarcoplasm of cardiomyocytes (mainly localized in inner mitochondrial membrane and outgoing cristae, sarcoplasmic reticulum).

Figure 14:
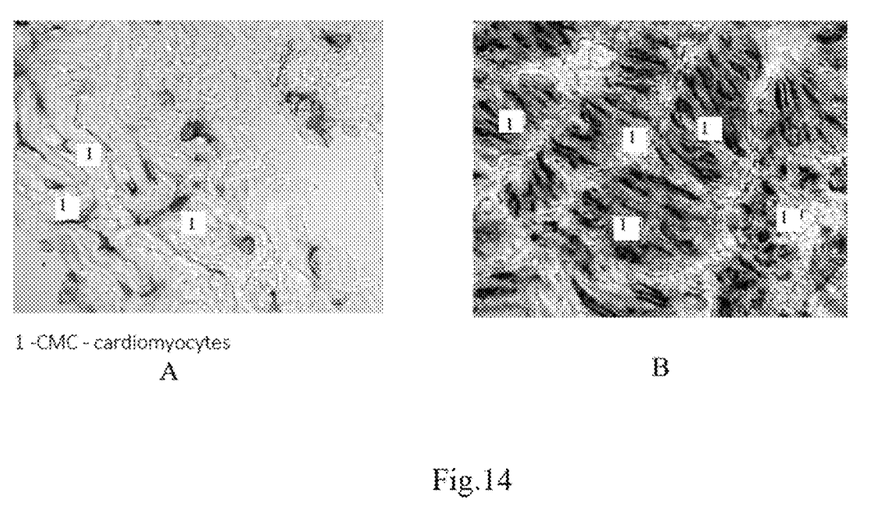
FIGS. 14-18 show micrograph images of tissues according to Example 1.

FIG. 14 shows micrographs characterizing the activity of lactate dehydrogenase detected in the sarcoplasm of cardiomyocytes germinating from LAA into porous PTFE coating of the clip jaws (a) and in the sarcoplasm of cardiomyocytes of the intact atrial appendage (b). Magnification ×400.

Mean LDH activity in LAA cardiomyocytes=95.06114±0.87 IU, which is significantly different from LDH activity of cardiomyocytes germinating in porous PTFE, mean value=72.94161±1.21 IU.

The decrease in LDH activity in cardiomyocytes germinating in porous PTFE, as compared with that of LAA cardiomyocytes, indicates a weakening intensity of the energy processes occurring in the myocardium under these conditions.

Figure 15:
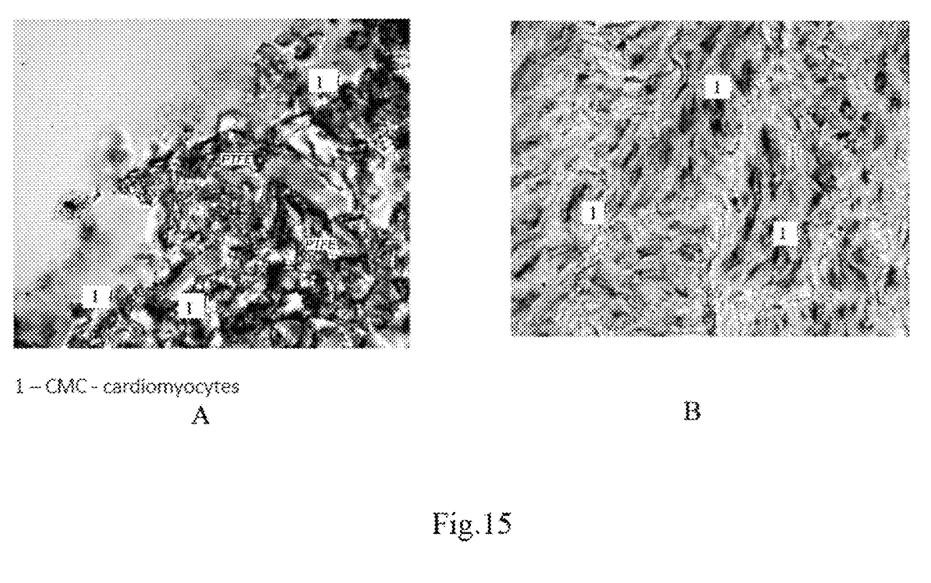

FIG. 15 shows micrographs characterizing the activity of succinate dehydrogenase detected in the sarcoplasm of cardiomyocytes germinating from LAA into porous PTFE coating of the clip jaws (a) and in the sarcoplasm of cardiomyocytes of the intact atrial appendage (b). Magnification ×400.

Mean SDH activity in cardiomyocytes germinating in porous PTFE=31.43±1.37 IU, which is significantly different from SDH activity of cardiomyocytes of intact LAA tissue, mean value=74.04391±1.08 IU.

A significant decrease in SDH activity in cardiomyocytes germinating in porous PTFE, as compared with that in LAA cardiomyocytes, indicates the inhibition of metabolic processes in the cardiac muscle, which are responsible for its energy supply under the test conditions. When analyzing the changes in LDH and LDH mean activity in cardiac myocytes of the intact atrial appendage and in cardiomyocytes germinating in porous PTFE, it can be clearly found that SDH activity in cardiomyocytes in all considered cases was significantly lower than LDH activity, which serves the manifestation of a lower metabolic activity of this enzyme in LAA cardiomyocytes. Lower values of SDH activity were reported in cardiomyocytes germinating in porous PTFE, which indicates a depressed functional activity of myocardium in this area.

Figure 16:
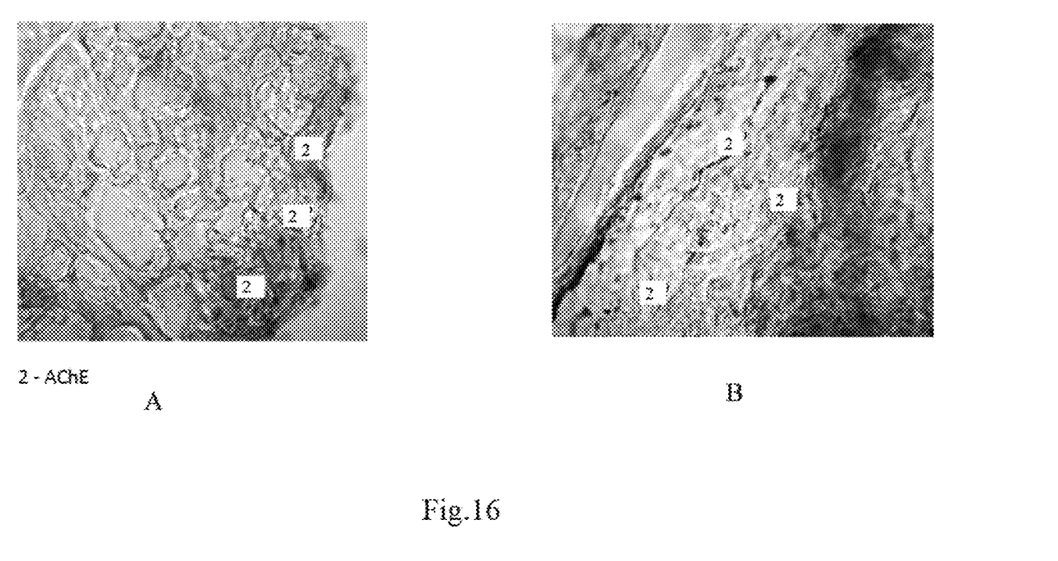

FIG. 16 shows micrographs characterizing AChE-positive nerve fibers in LAA myocardium, germinating in porous PTFE, Magnification ×400 (a), and AChE-positive nerve fibers in the intact atrial tissue, Magnification ×400.

Figure 17:
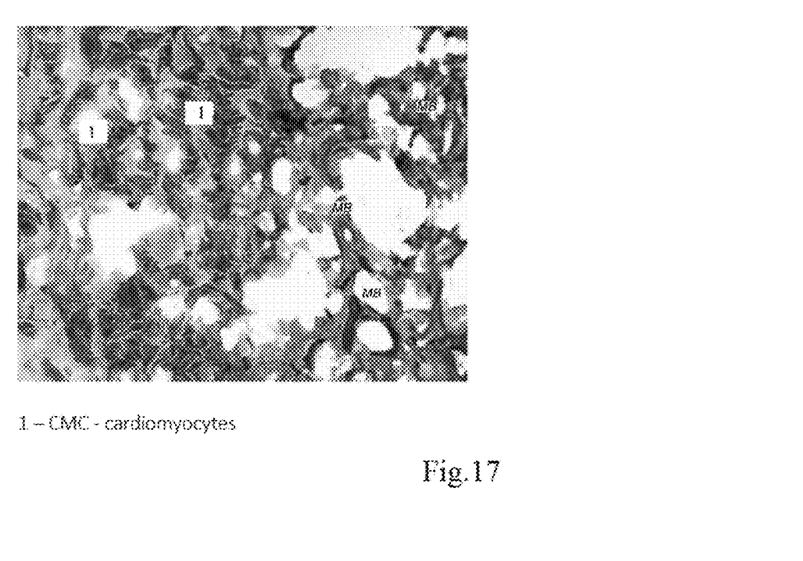

FIG. 17 shows micrographs characterizing the germination of LAA muscle fibers in porous PTFE. MF—muscle fiber. Staining by hematoxylin-eosin. Magnification ×250.

Figure 18:
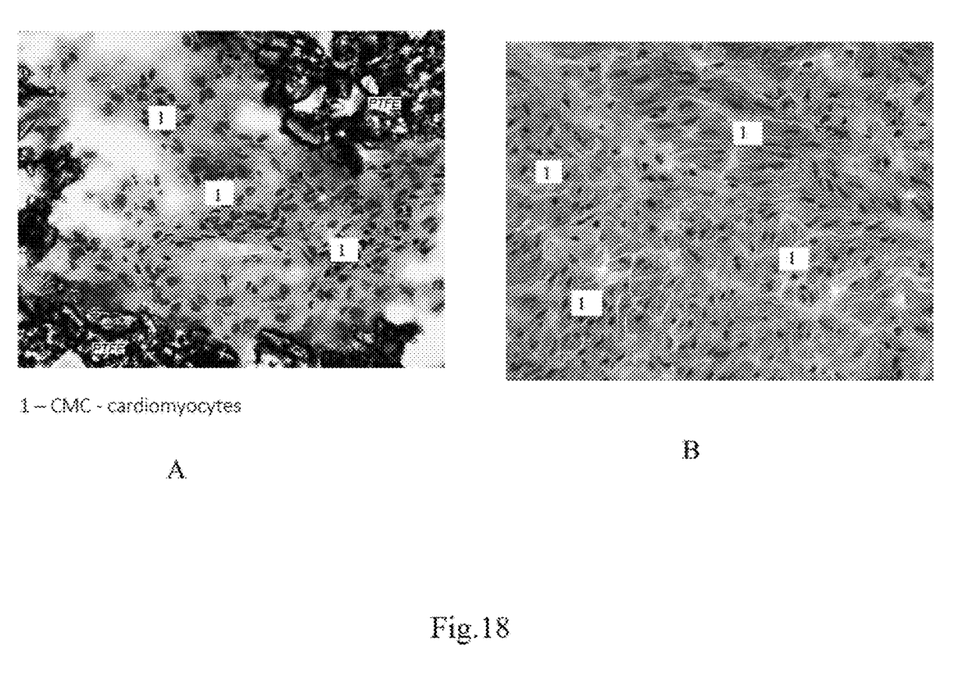

FIG. 18 shows micrographs characterizing (a) the germination of cardiomyocytes from the ear of the atrium in the porous PTFE (CMC—cardiomyocyte. Staining by hematoxylin-eosin. Magnification ×250) and (b) myocardial architectonics of intact LAA tissue (CMC—cardiomyocyte. Staining by hematoxylin-eosin. Magnification ×250).

Reference to the histological and histochemical studies of the atrial appendage with an implanted clip covered with porous PTFE, it can be concluded that:

LAA myocardial cells (cardiomyocytes, connective tissue, vessels) actively germinate into porous PTFE, as evidenced by hematoxylin-eosin staining of numerous muscle cells, vessels and connective tissue in the pores of PTFE, material covering the clip device;

LAA myocardium tissue, which germinates into porous PTFE, is functionally consistent, as evidenced by the energy metabolism enzymes identified in cardiomyocytes, i.e. lactate dehydrogenase and succinate dehydrogenase, being the indication of metabolic activity. Despite the fact that the enzyme activity is slightly lower compared to that in the reference sample (intact LAA tissue), it can be assumed that, for a longer period of LAA tissue clamping, cardiomyocytes germinating in porous PTFE will show more prominent metabolic activity due to structural and adaptive rearrangements caused by the presence of synthetic material;

LAA muscle tissue that grows into porous PTFE retains its cholinergic innervation, as evidenced by thin AChE-positive nerve fibers detected, which are visualized even in deeper layers of porous PTFE.

Thus, the claimed devices ensure a smooth and shockless effect of changeover of the first and second jaws from the diverged position to the clamped position with the control option of the impact force upon closing, as well as a mitigated impact of the clamped position over time.

What is claimed is:

1. A system for isolating left atrial appendage comprising:
a clip device formed by a first jaw and a second jaw which are parallel in their closed position and overlap each other in length, the clip device having a connecting device;
a clamping element comprising a first hinge;
the connecting device comprising a second hinge;
a clamping device connected a first end of the first jaw and a first end of the second jaw, the clamping device being configured to move the first and second jaws from their diverged position to a clamping position and to hold the first and second jaws in an extended or partially extended position at any angle ranging from 0° to 180 or in the clamping position;
a control device configured to implant the clip device so that a left atrial appendage is located between the first and second jaws; and
the first hinge being connected to the first end of the first jaw and the second hinge being connected to a second end of the first jaw, the first hinge and the second hinge being configured to rotate the first jaw relative to the second jaw at an angle ranging from 0° to 180°;
wherein the first hinge is made controllable and wherein the control device comprises a first hinge actuator adapted to couple detachably with tension to fit with the first hinge;
wherein the clamping element comprises a collet on the first hinge and a threaded lock nut mounted on an axis of the first hinge and configured to clamp the collet to avoid a relief motion; and
wherein the control device is made with a second actuator configured to be detachable with the threaded lock nut.

2. The system of claim 1, wherein the first end of the second jaw is rigidly fixed in the clamping element and a second end of the second jaw is rigidly fixed in the connecting device.

3. The system of claim 1, wherein each of the first and second jaws is made Π-shaped.

4. The system of claim 1, wherein the first and second jaws are made of biocompatible metal with a coating of porous polytetrafluoroethylene.

5. A system for isolating left atrial appendage comprising:
a clip device formed by a first jaw and a second jaw which are parallel in their closed position and overlap each other in length, the clip device having a connecting device;
a clamping element comprising a first hinge;
the connecting device comprising a second hinge;
a clamping device connected a first end of the first jaw and a first end of the second jaw, the clamping device being configured to move the first and second jaws from their diverged position to a clamping position and to hold the first and second jaws in an extended or partially extended position at any angle ranging from 0° to 180 or in the clamping position;
a control device configured to implant the clip device so that a left atrial appendage is located between the first and second jaws; and
the first hinge being connected to the first end of the first jaw and the second hinge being connected to a second end of the first jaw, the first hinge and the second hinge being configured to rotate the first jaw relative to the second jaw at an angle ranging from 0° to 180°;
wherein the first hinge is made controllable and wherein the control device comprises a first hinge actuator adapted to couple detachably with tension to fit with the first hinge; wherein a first actuator of the control device is a first elongated cylindrical element for applying rotational motion to the first hinge with optional controlled rotation of the first jaw relative to the second jaw, and wherein a second actuator of the control device is a second elongated cylindrical element being a concentric tube installed over the first elongated cylindrical element to apply rotational motion on a threaded lock nut.

6. The system of claim 5, wherein the first actuator and the second actuator of the control device are equipped with first and second levers fixed at a 90° angle, respectively, the first and the second levers each shaped as a torque arm with an option of controlled rotation of the respective actuator.

7. The system of claim 5, wherein the first elongated cylindrical element and the second elongated cylindrical element are curved.

8. A clip device for isolating left atrial appendage, the clip device comprising:
a first jaw and a second jaw which are parallel in their closed position and overlap each other in length;
a clamping element comprising a first hinge;
a connecting device comprising a second hinge;
a clamping device being installed between a first end of the first jaw and a first end of the second jaw, the clamping device being configured to move the first and second jaws from a diverged position to a clamping position and to hold the first and second jaws in an extended or partially extended position at any angle ranging from 0° to 180 or in the clamping position; and
the first hinge being connected to the first end of the first jaw and the second hinge being connected to a second end of the first jaw, the first hinge and the second hinge being configured to rotate the first jaw relative to the second jaw at an angle ranging from 0° to 180°;
wherein the first hinge is made controllable and being adapted to couple detachably with tension to fit with the first hinge, and wherein the clamping element comprises a collet on the first hinge and a threaded lock nut mounted on an axis of the first hinge and configured to clamp the collet to avoid a relief motion.

9. The clip device of claim 8, wherein the first end of the second jaw is rigidly fixed in the clamping element and a second end of the second jaw is rigidly fixed in the connecting device.

10. The clip device of claim 8, wherein each of the first and second jaws is made Π-shaped.

11. The clip device of claim 8, wherein the first and second jaws are made of biocompatible metal with a coating of porous polytetrafluoroethylene.

* * * * *